United States Patent

Dannenhauer et al.

(10) Patent No.: US 6,303,050 B1
(45) Date of Patent: Oct. 16, 2001

(54) COMPOUNDS, PROCESS FOR THEIR MANUFACTURE, AS WELL AS A PROCESS FOR MANUFACTURING LIQUID-CRYSTALLINE POLYMERS USING THESE COMPOUNDS

(75) Inventors: Fritz Dannenhauer, Ulm; Michael Gailberger, Neu-Ulm; Karl Holdik; Katja Strelzyk, both of Ulm; Kathrin Kuerschner, Bayreuth; Andreas Stohr, Kriftel; Peter Strohriegl, Bayreuth, all of (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/465,776

(22) Filed: Dec. 17, 1999

Related U.S. Application Data

(62) Division of application No. 09/055,303, filed on Apr. 6, 1998, now abandoned.

(30) Foreign Application Priority Data

Apr. 5, 1997 (DE) ............................................. 197 14 119

(51) Int. Cl.⁷ .................................................. C09K 19/52
(52) U.S. Cl. ................... 252/299.01; 522/170; 522/181; 526/318.25
(58) Field of Search ...................... 252/299.01; 522/170, 522/181; 526/318.25

(56) References Cited

FOREIGN PATENT DOCUMENTS

| | | |
|---|---|---|
| 4342280 A1 | 6/1995 | (DE) . |
| 4405316 A1 | 8/1995 | (DE) . |
| 44 08 170 | 9/1995 | (DE) . |
| 4408170 A1 | 9/1995 | (DE) . |
| 4408171 A1 | 9/1995 | (DE) . |
| 195 20 704 A1 | 12/1996 | (DE) . |
| 19525941 A1 | 1/1997 | (DE) . |
| 0675186 A1 | 3/1995 | (EP) . |
| 0699731 A2 | 8/1995 | (EP) . |
| 0700981 A2 | 9/1995 | (EP) . |
| 0731084 A2 | 2/1996 | (EP) . |
| 0755915 A2 | 7/1996 | (EP) . |
| WO 96/24647 | 8/1996 | (EP) . |
| 837054 | 4/1998 | (EP) . |
| 0 869 112 | 10/1998 | (EP) . |
| 4-31405 | 2/1992 | (JP) . |
| 7-102019 | 4/1995 | (JP) . |
| 8-104870 | 4/1996 | (JP) . |
| 8-028777 | 8/1996 | (JP) . |
| 9-20781 | 1/1997 | (JP) . |
| WO 97/00600 | 1/1997 | (WO) . |
| WO97/23580 * | 7/1997 | (WO) . |

OTHER PUBLICATIONS

Römpplexikon, Chemie, 10. Auflage (p. 5106).
Brockhaus Enzyklopädie, 19. Auflage, 12. Band, KIR–LAG (p. 237).
Brockhaus Enzyklopädie, 19. Auflage, 24. Band, Wek–Zz (p. 634).
J. M. Cowie, H.W. Hunter, *Makromol. Chem.* 191, 1393–1401 (1990).
B. Otterholm, C. Alstermark, K. Flatischler, A. Dahlgren, S. T. Lagerwall & K. Skarp *Mol. Cryst, Liq. Cryst.*, 146 189–216 (1987).
S. Jarohmi, J. Lub, G.N. Mol, *Polymer* 35, 622 (1994).
D. J. Broer, J. Boven, G.N. Mol. *Makromol. Chem.* 190, 2255 (1989).
J. M. G. Cowie, H.W. Hunter, *Makromol. Chem.* 192, 143 (199).
J. Lub, D.J. Broer, R. A. M. Hikmet, K. G. J. Nierop, *Liquid Crystals* 18/2 319–236 (1995).
D.J. Boer, J. Lub, G.N. Mol. *Macromolecules* 26, 1244–1247 (1993).
R. A. M. Hikmet, J. Lub., J. A. Higgins, *Polymer* 34, 1739 (1993).

* cited by examiner

*Primary Examiner*—Jill Warden
(74) *Attorney, Agent, or Firm*—Crowell & Moring LLP

(57) ABSTRACT

A compound for use as a nematic phase in cholesteric liquid polymers of the general formula C—$A_m$, and a production process.

19 Claims, 7 Drawing Sheets

COMPOUNDS, PROCESS FOR THEIR MANUFACTURE, AS WELL AS A PROCESS FOR MANUFACTURING LIQUID-CRYSTALLINE POLYMERS USING THESE COMPOUNDS

This application is a division of application Ser. No. 09/055,303, filed Apr. 6, 1998 now abandoned.

BACKGROUND AND SUMMARY OF THE INVENTION

This application claims the priority of 197 14 119.6, filed Apr. 5, 1997, the disclosure of which is expressly incorporated by reference herein.

The invention relates to compounds, to a process for their manufacture as well as to a process for manufacturing liquid-crystalline polymers using these compounds.

Liquid-crystalline polymers are used mainly in the manufacture of polymer coatings and colored paints.

Polymer coatings and colored paints are very important for coating surfaces and the aesthetic designing of objects. Many different color impressions and particularly color effects, can be achieved in various ways. Current polymer coatings contain particles or pigments in a carrier polymer for providing color or special effects, such as metallic gloss. In order to achieve certain reflection effects, for example, metal tinsels, coated mica particles or interference pigments on the basis of liquid-crystalline compounds are worked into a clear paint body as the carrier polymer. For a free design of the color impression, additional other pigments may also be added.

Another possibility of effectively providing color consists of the use of liquid-crystalline polymers, copolymers, oligomers (macromonomers) or monomers. Some of these liquid-crystal materials are suitable for forming cohesive polymer films. They polymerize in the liquid-crystal phase and, in the process, produce a paint layer with a special color effect. A working into a carrier material, for example, into a clear paint, is not required.

In principle, numerous substances are known which show a liquid-crystalline state. These are, as a rule, elongated organic molecules which are suitable for taking up a certain molecular order condition. As a function of the order condition of the liquid-crystalline phase, only those wavelengths are reflected by the impinging light which interfere with the equidistant interplanar spacing of the liquid-crystalline materials. This produces certain color and reflection effects. The formation of certain liquid-crystalline phases takes place in defined temperature ranges whose position and width, in turn, depend on the chemical structure of the materials. In addition, color appearance of the liquid-crystal phases within the phase is frequently a function of the temperature; that is, during the heating and cooling of the liquid-crystalline phase, different wavelengths are reflected. In order to produce paints or other polymer coatings which have certain wavelength reflections and light effects, it is therefore necessary to fix or mechanically stabilize the liquid-crystalline phase. As a result, certain color or reflection effects can be durably retained. A liquid-crystalline phase can be fixed by a polymerization or chemical cross-linking of the starting molecules to form a dense network. For this purpose, the starting materials must contain cross-linkable reactive groups.

From the literature, liquid-crystalline monomer compounds are known which have two identical terminal reactive groups:

J. Lub, D. J. Broer, R. A. M. Hikmet, K. G. J. Nierop, *Liq. Cryst.* 18/2, 319 (1995);

D. J. Broer, J Lub, G. N. Mol, *Macromolecules* 26, 1244 (1993);

R. A. M. Hikmet, J. Lub, J. A. Higgins, *Polymer* 34, 1736 (1993);

S. Jarohmi, J. Lub, G. N. Mol, *Polymer* 35, 622 (1994). As a rule, the cross-linking of such monomers takes place photochemically by photocyclo-addition or with the addition of a photoinitiator to the monomer mixture. Likewise, thermally initiated radical cross-linkages or thermally initiated addition or condensation reactions are known. For forming a polymer film, the known liquid-crystal monomers are applied to the corresponding substrates and the polymerization reaction is initiated, in which case the terminal groups polymerize simultaneously and the finished end product is created.

The application and adhesiveness of the starting monomers on the substrate to be coated may cause serious difficulties. As a rule, liquid crystal monomers are crystalline, which is why their adhesiveness on the substrate is poor. Furthermore, application of a uniform thickness layer is difficult. In addition, with respect to the hardness, elasticity and adhesion of the end product, specifically of the polymer film, the known liquid-crystal materials are relatively invariable and unable to adapt to the requirements of certain applications.

From German Patent Application 196 43 048.8, filed on Oct. 18, 1996, liquid-crystalline compounds are known which have various terminal polymerizable radicals. During polymerization, these compounds permit a two-step process because the different reactive radicals can be cross-linked by polymerization reactions of different initiation and reaction mechanisms. As a result, prepolymers can first be produced in the form of homopolymers or copolymers with polymerization straight lines (oligomers) which are not excessive. These prepolymers can be handled more easily than the monomers themselves.

However, it is still a disadvantage in this case that the range of the compositional variation of the prepolymers is limited or hard to control. Furthermore, the transition temperature will rise with the degree of polymerization, and this is not advantageous for all applications.

It is therefore an object of the invention to provide compounds and a process for their manufacture as well as a process for manufacturing liquid-crystalline polymers on the basis of these compounds which have a larger range of variational composition while they can be handled better and permit better control of the composition.

This object is achieved by compounds and a process for their manufacture for use as a nematic phase in cholesteric liquid polymers of the general formula C—$A_m$, wherein $m \geq 2$, such that when m=2, C is a radical of the general formula $C_nH_{2n}$, in which n is a whole number from 1 to 40 and at least one methylene group may be substituted by oxygen or at least one hydrogen may be substituted by alkyl or alkoxy groups, said alkyl or alkoxy groups having 1 to 20 carbon atoms, when m>2, C is a branched and multifunctional radical and is selected from the group consisting of oligopropylene oxide, oligobutylene oxide, branched alkyls with 4 to 40 Carbon atoms, trimethylol propane, pentaerythrite, cyclohexane tricarboxylic acid, cyclohexane triole, aromatic carboxylic acids with two carboxyl groups and phenolene with at least two OH—groups, wherein A are identical or different radicals of the general formula Y—B—M, wherein Y is a polymerizable radical, B are identical or different radicals of the general formula $C_nH_{2n}$, in which n is a whole number from 0 to 20 and at least one methylene group may be substituted by oxygen, and M has the general formula $R^1$—$X^1$—$R^2$—$X^2$—$R^3$—$X^3$—$R^4$—, wherein $R^1$, $R^2$, $R^3$ and $R^4$ are identical or different double-bonding radicals selected from the group consisting of —O—, —COO—, —CONH, —CO—, —S—, —C≡C—, —CH=CH—, —CH=N—, —CH$_2$—, —N=N—, and —N=N(O) and $R^2$—$X^2$—$R^3$, $X^3$—$R^4$ or $R^2$—$X^2$—$R^3$—$X^3$ may be a C—C bond, $X^1$, $X^2$, and $X^3$ are identical or different radicals selected from the group consisting of 1,2-, 1,3- or 1,4-phenylene, and 1,2-, 1,3- or 1,4-cyclohexene with at least one B radical being a substituted aryl alkane or heteroaryl alkane with 6 to 10 atoms in the aryls core, the substitution being from 1 to 3 heteroatoms selected from the group consisting of O, N, and S, and another at least one B radical being a substituted 3 to 10 carbon cycloalkane, said substituted group of the another at least one B radical being at least one identical or different substituent selected from the group consisting of —H, linear or branched $C_1$- to $C_{20}$-alkyl, $C_1$- to $C_{20}$-alkoxy, $C_1$- to $C_{20}$-alkylthio, $C_1$- to $C_{20}$-alkyl carbonyl, $C_1$- to $C_{20}$-alkoxycarbonyl, $C_1$- to $C_{20}$-alkylthiocarbonyl, —OH, —F, —Cl, —Br, —I, —CN, —NO$_2$, cycloalkyl, formyl, and linear or branched alkyl, alkoxy or alkylthio radicals with 1 to 20 carbon atoms which are interrupted by ether oxygen, thioether sulfur or ester groups.

A composition may contain mixtures of these compounds.

The cross-linking of two liquid-crystalline units A by way of a radical (denoted below as a spacer) therefore results in twin nemates; the cross-linking of several liquid-crystalline units A results in star nemates; star nemates, thus, have a higher degree of cross-linking. In this manner, monomers are obtained whose mol masses are already in the molecular weight range of oligomers and which solidify in a glass-type manner.

The compounds according to the invention have the advantage that they are monomers with a defined structure and have mol masses in the range of oligomers (1,000 to 3,000 g/mol). Despite the high mol mass, the monomers have low viscosity and can therefore easily be oriented in the liquid-crystalline phase. This good orientation is also maintained after cross-linking. This is demonstrated by narrow absorption bands of the formed polymer films in the UV-VIS-absorption spectrum (half-width values in the range of 50 mm). If, in addition, the HTP (HTP= Helical Twisting Power) of conventional monomers is compared with the compounds according to the invention, the latter can be twisted just as well. This applies particularly to those compounds with m=2 (denoted hereinafter as a twin nemate; compare also FIG. 1) and also to those where m is greater than or equal to 3 (denoted hereinafter as a star nemate; compare also FIGS. 2a and 2b).

In contrast to conventional monomers, the compounds according to the invention have a considerably larger range of compositional variation which can be utilized for polymerization. Different liquid-crystalline units are cross-linked with one another in a targeted manner. Thus, according to the invention, compounds of a defined structure can be used in a planned manner for building up liquid-crystalline polymers and thus for controlling the characteristics of these polymers. In this manner, a much larger number of polymers are available which can be polymerized into the polymer network.

The inserting of flexible elements into the radical B (denoted hereinafter as a side chain) and in the spacer, C, causes a lowering of the transition temperatures so that these can be adapted in a targeted manner to the respective desired application.

In contrast to the state of the art, it is therefore possible to produce monomeric units of a higher molecular weight and a desired composition in a targeted manner, and thus influence the characteristics of the monomers and of the resulting polymer film in a targeted manner. In particular, material parameters, such as the viscosity, film forming characteristics, course, flow properties, solubility, color, gloss, cooling, working properties, adhesion, elasticity, hardness, etc. can be adjusted in a targeted fashion.

The monomers according to the invention can be easily processed and, in comparison to the known polycrystalline monomers and the known prepolymers, have clearly improved application properties. By way of the composition of the compounds according to the invention, for example, the viscosity can be influenced and thus the behavior during the application to the substrate to be coated. Adhesion of the end product on the substrate can be adapted by way of the polymerization step, for example, by the concentration of the reactive Y groups to the respective substrate.

Particularly advantageous liquid crystal monomers are those with m=2, 3 or 4. These are the mentioned twin nemates and star nemates (compare FIGS. 1, 2a and 2b). These compounds can be handled easily and can also be synthesized at relatively low cost since they contain a clear number of mesogeneous units.

It is useful for the number n of the carbon atoms of the B radicals to be 1 to 10, preferably 2 to 6. It is also preferred for the radicals $R^1$, $R^2$, $R^3$ and/or $R^4$ to be —O—, —COO— or $CH_2CH_2O$—, since these promote the liquid-crystalline properties. The same applies if $R^2$—$X^2$—$R^3$ is a C—C bond and/or if the radicals $X^1$ and/or $X^3$ are 1,4-phenylene or 2-methoxy 1,4-phenylene. The latter may also be considered a vanillin unit (4-hydroxy-3-methoxy benzaldehyde). The radicals $X^1$, $X^2$ and $X^3$ may also be multiple-substituted. Preferred embodiments are 3,4-dihydroxy benzoic acid and 3,5-dimethoxy-4-hydroxy benzoic acid.

A preferred embodiment of the compound according to the invention contains a tetraethylene glycol radical, a butyl radical or a hexyl radical as the spacer C. The side chains B are preferably hexyl radicals or ethylene oxide radicals.

The polymerizable radical Y is an acrylate radical, a methacrylate radical, a vinyl ether radical, an epoxide radical or an azide radical.

The process according to the invention is distinguished by three reaction steps: First a mesogen of the general formula Y—B—M' is synthesized, M' having the general formula —$R^1$—$X^1$—$R^2$—$X^2$—$R^3$—. In this case, $R^3$ carries a reactive terminal group. In parallel thereto, a linear or branched spacer C' is synthesized which has the radical C as well as terminal functional groups, particularly radicals M" of the general formula $X^3$—$R^4$. In a last step, these two compounds are synthesized by way of their terminal reactive groups to form the compound according to the invention.

Thus, by means of the appropriate selection of the adducts, the mesogeneous units M, the side chains B, the reactive radicals Y and the spacers of the compounds according to the invention can be selected in a targeted manner and can be assembled. In this fashion, "made-to-measure" compounds can be obtained which have characteristics which are optimal for the respective usage.

The reaction of the individual adducts in steps a) and b) to the desired intermediates takes place in the known classical manner by way of terminal reactive groups. In step c), the intermediate products are assembled to the compound according to the invention, preferably by way of an esterification.

For the application and in order to be able to apply the compounds as a paint to a substrate to be coated according to the invention, it is particularly expedient to dissolve them in an organic solvent, preferably in chloroform or tetrahydrofurane, and to evaporate the solvent before the actual reaction. The form of the compounds according to the invention which is to be applied can thus be adapted to the most varied application requirements. The compounds can also be marketed in the solvent. Furthermore, solutions of the compounds according to the invention can be produced in arbitrary concentrations with defined viscosity properties, spreading properties, wetting and adhesion properties.

Application to the substrate to be coated can take place in any suitable manner. Thus, surfaces may be sprayed or painted or may be dipped into the solution of the compounds according to the invention. According to conditions and the solvent, the solvent may be evaporated at room temperature or at a raised temperature, at a vacuum or in an air current. At raised is temperatures, it should be taken into account that the polymerization reaction in the case of certain compositions may start which, however, may also be advantageous for individual applications.

The process for manufacturing the liquid-crystalline polymers from the compounds according to the invention comprises cross-linking the compounds according to the invention by way of their terminal Y radicals. In the case of a preferred embodiment, the polymerization takes place radically or cationically by way of acrylate or methacrylate groups and by way of vinyl ether groups, epoxide groups or azide groups. It is particularly advantageous to add polymerization initiators, preferably photoinitiators. Classical radical initiators are, for example, 2,2-dimethoxy-2-phenyl acetophenone, 2,2'-azobis-(2-methyl propionitrile), dibenzoyl peroxide or di-t-butyl peroxide. Initiator concentrations of from 1 to 5 molar percent are particuarly preferred. For the radical polymerization reaction, the presence of a reaction control substance is also advantageous, preferably 1-capric thiole (1-decanthiol), particularly preferably at a reaction control concentration of 1 to 10 molar percent. As a result of the use of a radical polymerization initiator and optionally the addition of a reaction control substance, the reaction conditions can be optimized.

The polymerization while reacting the vinyl ether, epoxide or azide groups is carried out in the presence of at least one polymerization initiator, preferably a cationic photoinitiator. The photoinitiator is expediently present at a quantity of from 0.5 to 10% by weight, preferably at 1 to 5% by weight. It preferably contains a diaryl sulfonium salt, a diaryl iodonium salt or a mixture thereof. Examples of such photoinitiators are the commercially available products Degacure KI 85 (Degussa), Bis (4-tert.butylphenyl) iondonium hexafluorophosphate (Midori Chemical), 2,4,6-trimethyl benzoyl ethoxyphenyl phosphine oxide (BASF) in a mixture with diphenyl iodonium hexafluorophosphate and 2,2-dimethoxy-2-phenyl acetophenone in a mixture with diphenyl iodonium tetrafluoroborate. In addition, the polymerization reaction can be induced by ultraviolet radiation and/or the reaction product can be aftercured by thermal treatment.

The use of a photoinitiator offers special advantages because it can more easily start, regulate and optionally accelerate the reaction to the end product. In contrast to the purely thermal hardening, the induction of the polymerization reaction by ultraviolet radiation saves considerable energy costs and can more rapidly be used in a targeted manner and can be metered better. The thermal treatment has advantages when, because of shading or inaccessibility, the surface to be coated cannot be reached by the initiation radiation.

In a particularly preferred embodiment of the process according to the invention, the polymerization is carried out in the presence of at least one additional compound according to the general formula of at least one of $Y^3$—$B^3$—$M^2$—$B^4$—$Y^4$ and $(Y^3$—$B^3)_n$—$M^2$—$B^4$—$Y^4$, wherein n is equal to 2 or 3, $Y^3$ is a polymerizable radical and $Y^4$ is a polymerizable radical or a non-polymerizable radical selected from the group consisting of —H, —CN and a cholesteryl group, $B^3$ and $B^4$ are identical or different radicals of the general formula $C_nH_{2n}$, wherein n is a whole number from 0 to 20 and at least one methylene group may be substituted by oxygen, M has the general formula —$R^5$—$X^4$—$R^6$—$X^5$—$R^7$—$X^6$—$R^8$, wherein $R^5$, $R^6$, $R^7$, and $R^8$ are identical or different double-bonding radicals selected from the group consisting of —O—, —COO—, —CONH, —CO—, —S—, —C C—, —CH=CH—, —CH=N—, —CH$_2$—, —N=N—, and —N=N(O) and $R^6$—$X^5$—$R^7$ or $R^6$—$X^5$—$R^7$—$X^6$ may also be a C—C bond, $X^4$, $X^5$ and $X^6$ are identical or different radicals selected from the group consisting of 1,2-, 1,3- or 1,4-phenylene and 1,2, 1,3- or 1,4-cyclohexene with at least one B radical being a substituted aryl alkane with 6 to 10 atoms in the aryl core with the substitution being from 1 to 3 heteroatoms selected from the group consisting of O, N, and S, and another at least one B radical being a substituted 3 to 10 carbon cycloalkane, said substituted group of the another at least one B radical being at least one identical or different substituent selected from the group consisting of —H, linear or branched $C_1$- to $C_{20}$-alkyl, $C_1$- to $C_{20}$-alkoxy, $C_1$- to $C_{20}$-alkylthio, $C_1$- to $C_{20}$-alkyl carbonyl, $C_1$- to $C_{20}$-alkoxycarbonyl, $C_1$- to $C_{20}$-alkylthiocarbonyl, —OH, —F, —Cl, —Br, —I, —CN, —NO$_2$, cycloalkyl, formyl, and linear or branched alkyl, alkoxy or alkylthio radicals with 1 to 20 carbon atoms which are interrupted by oxygen, thioether sulfur or ester groups. These additional compounds—denoted hereinafter as comonomers—are particularly suitable for adapting the characteristics of the polymerization end product to the corresponding application requirements. The adjustable mechanical characteristics of the end product are particularly adhesiveness, elasticity and the hardness of the polymer film on the corresponding substrate.

The use of comonomers according to the invention is particularly advantageous for influencing the visual effect of the polymer film. By admixing chiral constituents to an active nematic substance, a cholesteric phase can be induced. This is particularly advantageous when the liquid-crystalline characteristics of the host substance are not very pronounced. In this respect, the chiral constituent causes a reinforcing effect. Subsequently, this mixture is photolinked while a suitable initiator is added in the liquid-crystalline phase. In this manner, the cholesteric phase can be frozen in the network.

In this case, it is particularly expedient for radicals $B^3$ and/or $B^4$ to be chiral. By using one or several chiral or chiral-nematic comonomers in different mixing ratios with the compounds according to the invention, arbitrary reflection wavelengths of the polymer films from the ultraviolet to the infrared range can be adjusted. The copolymerization of highly cross-linked nematic constituents with a polymerizable chiral monomer results in high cross-linking densities. In these highly cross-linked polymer films, the reflection wavelength does not depend on the temperature.

Examples of comonomers suitable according to the invention are the following compounds:

4-[(S)-(2-Acryloyloxy-2-methyl)-ethyloxyl]-4'-cyanobiphenyl

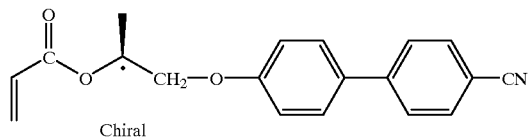

4-[S]-(2-Acryloyloxy-2-methyl)-ethyloxy]-4'-[(S)-2-methylbytyloxy]-biphenyl cal characteristics of the end product. During the polymerization reaction, such copolymers result in chain breaks and thus regulate the degree of cross-linking. The chiral centers of the comonomers promote the forming of a cholesteric phase in the liquid-crystalline polymer. Such a cholesteric structure, which can be implemented only by means of visually active molecules and represents a type of superstructure of the individually constructed liquid-crystalline textures, contains liquid-crystalline elementary areas in a helical arrangement. The height of the individual helical elementary areas—also called "lead"—determines the wavelength of the reflected light and therefore the colors of the metallically opalescent reflexes.

Other examples of comonomers according to the invention, which promote a cholesteric phase, are cholesterin derivatives, such as the following compounds:

Cholesteryl-4-(2-vinyloxyethoxy)-benzoate

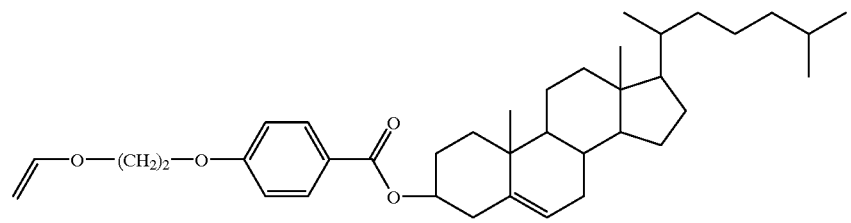

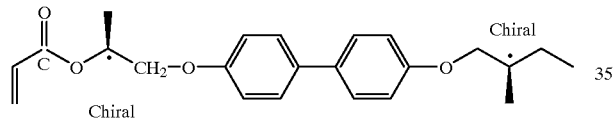

{4'-[S-(2-Acryloyloxy-2-methyl)-ethyloxy]-phenyl}-4-2-vinyloxyethoxy)-benzoate

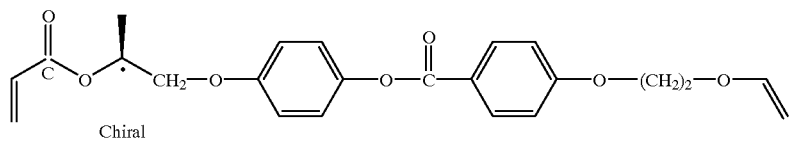

R, S-Di-(4' (3-acryloyloxy-2'methylpropoxyl) benzoic acid] 1,4 phenyl diester

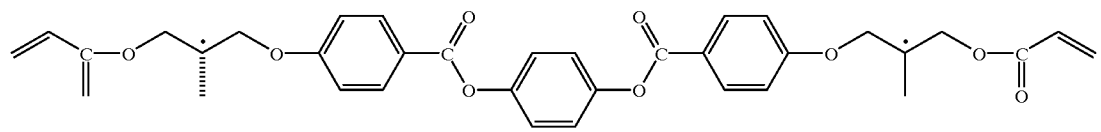

The copolymers preferably have one or two polymerizable radicals $Y^3$, such as acrylate or methacrylate groups. Copolymers with only one polymerizable radical, in addition to influencing the visual effect, also affect the mechani- Cholesteryl 4-(6-acryloyloxyhexyloxy)-benzoate
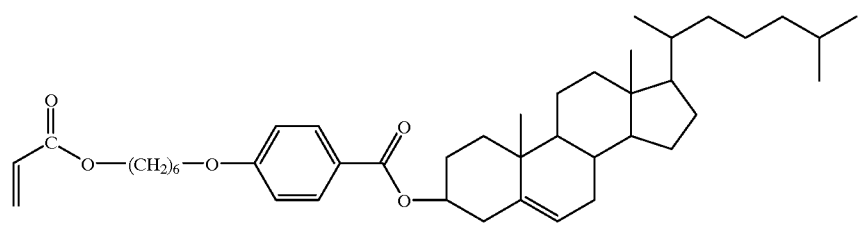
Cholesteryl-3,4-di-(1-vinyloxyethoxy)-benzoate
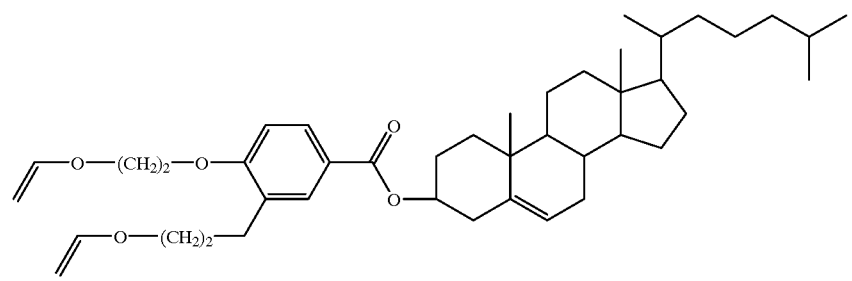
Cholesteryl-3,4-di-(6-acryloyloxyethyloxy)-benzoate
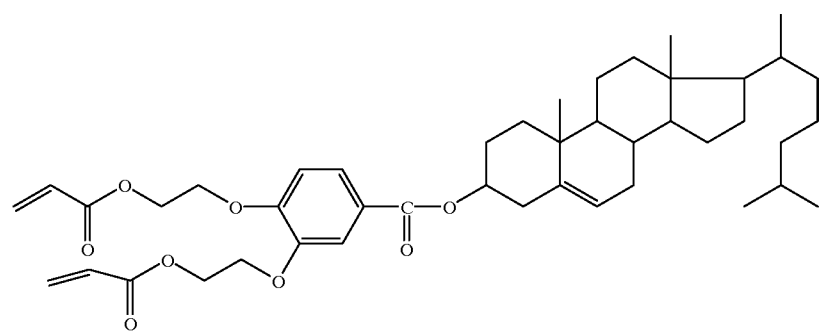
Another suitable compound group are derivatives of 1,4:3,6-dianhydro-D-mannite, as, for example, the following compound with two vinyl ether groups:
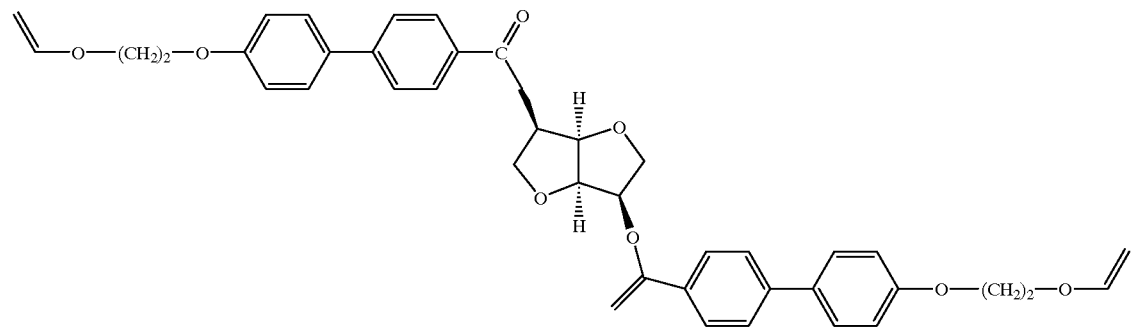

Other objects, advantages and novel features of the present invention will become apparent from the following detailed description of the invention when considered in conjunction with the accompanying drawings.

DETAILED DESCRIPTION OF THE DRAWINGS

Figure 1:
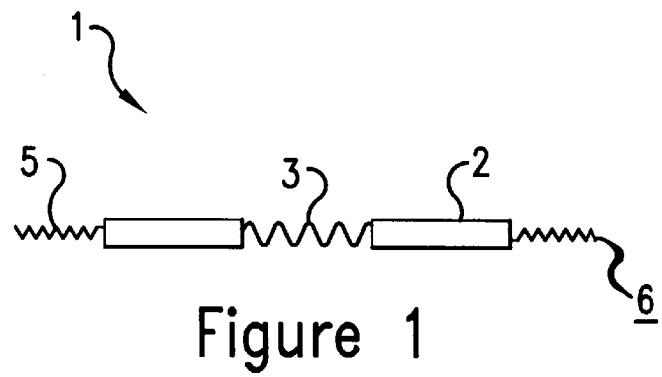
FIG. 1 is a schematic representation of a twin nemate according to the invention.
Figure 2A:
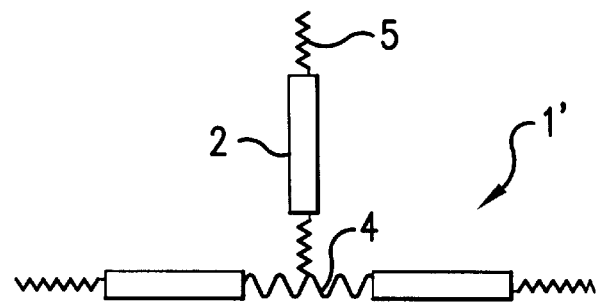
FIG. 2a is a schematic representation of a star nemate with m=3, according to the invention.
Figure 2B:
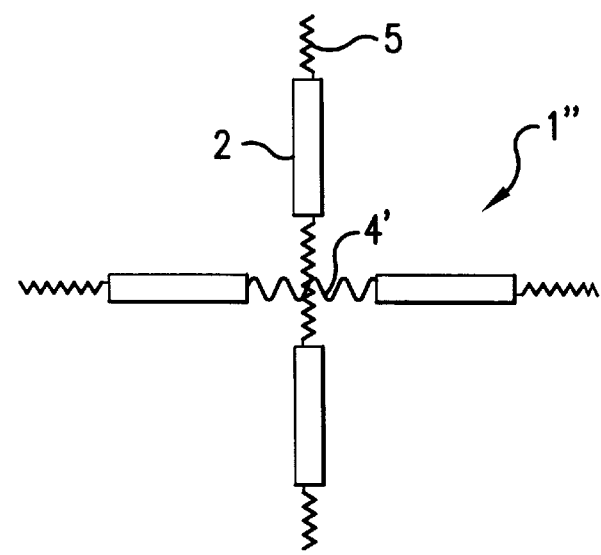
FIG. 2b is a schematic representation of a star nemate with m=4 according to the invention.

FIGS. 1, 2a and 2b are schematic representations of a twin nemate 1 and of a star nemate 1' and 1" according to the invention. Two, three or four mesogeneous units 2 (corresponding to the formula symbol M) are linked with one another by way of a linear spacer 3 or a branched spacer 4 or 4' (corresponding to the formula symbol C). The free ends of the mesogeneous units 2 carry side chains 5 with polymerizable terminal groups 6 (corresponding to the formula symbols B and Y).

EXAMPLE 1

A first embodiment in the present invention has the following structure:

(Twin Nemate 1)

Figure 3A:
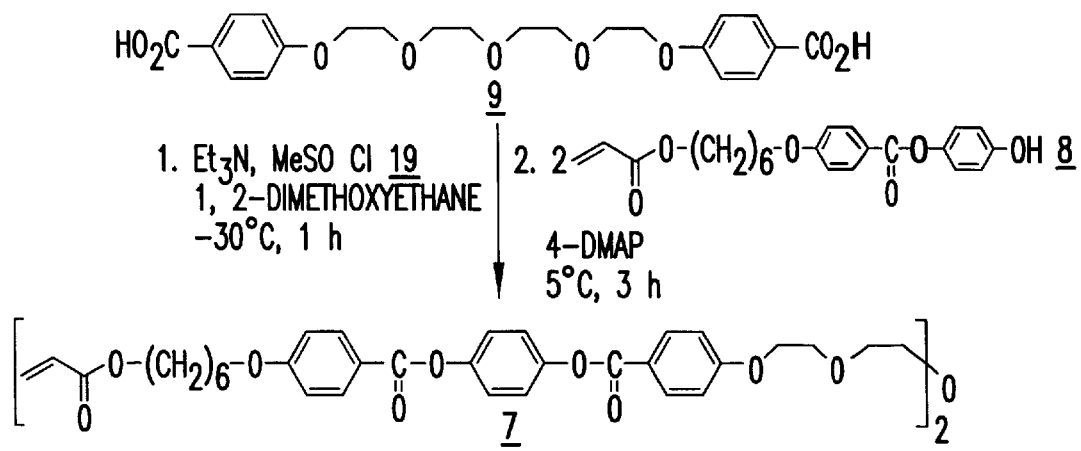
FIG. 3a is a schematic representation of the synthesis for a first embodiment of a three-core twin nemate with an alkyl side chain.

According to the diagram illustrated in FIG. 3a, this compound can be synthesized as follows:

1.30 g (0.003 mol) tetraethylene glycol-1,13-bis-(4-benzoic acid) are reduced to slurry in 100 ml 1,2-dimethoxy ethane and, after the addition of 1.7 ml (0.012 mol) $Et_3N$ are cooled to −30° C. At −30° C., 0.47 ml (0.006 mol) methane sulfonic acid chloride are now added in drops such that the temperature does not exceed −25° C. After 1 h of stirring at −30° C., 2.54 g (0.0066 mol) of 4-(6-acryloyloxy hexyloxy) benzoic acid-4'-hydroxy-phenylester, 0.081 g (6,6×10$^{-4}$ mol) r-dimethylamino pyridine and 50 mg 2,6-Di-tert-butyl-p-cresol are added as the stabilizer and the stirring takes place for another 3 h at 5° C.

Then, the precipitation is filtered off, is washed twice with 20 ml respectively of 1,2-dimethoxy ethane and twice with 20 ml respectively of $CHCl_3$. The filtrate is concentrated in the WV; the residue is dried in the vacuum and is recrystallized in 50 ml isopropanol. The further cleaning of the product takes place by column chromatography by way of silica gel with $CHCl_3$/ethyl acetate 1:2 as the flow medium. As a residue, 1.79 g (51%) twin nemate 1 is obtained in the form of white crystals.

Figure 3B:
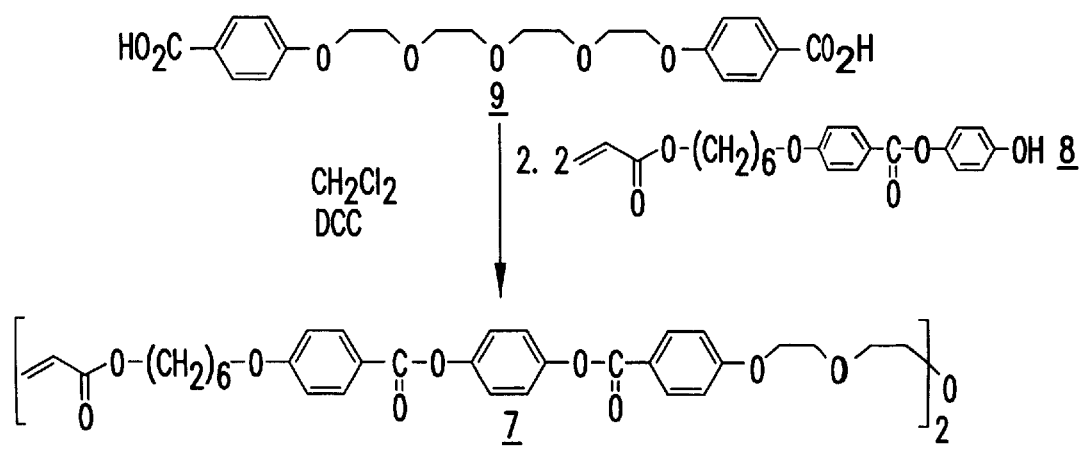
FIG. 3b is a schematic representation of the synthesis for a first embodiment of a three-core twin nemate with an alkyl side chain.

The synthesis can also be carried out according to the following specification (compare the synthesis diagram illustrated in FIG. 3b):

0.87 (0.002 mol) tetraethylene glycol-1,13-bis-(4-benzoic acid), 1.54 g (0.004 mol) mesogen (=4-(6-acryloyloxy-hexyloxy) benzoic acid-4'-hydroxy-phenyl ester), 0.059 g (4.8×10$^{-4}$ mol) 4-DMAP and 50 mg 2,6-Di-tert-butyl-p-cresol are dissolved in 50 ml $CH_2Cl_2$ and cooled to 0° C. At 0° C., 0.99 g (0.0048 mol) DCC are added; stirring takes place for 30 min. at 0° C. and overnight at room temperature.

The formed precipitation is filtered off. The $CH_2Cl_2$-phase (filtrate) is washed twice with 25 ml of a 2NHCl solution and once with 25 ml of a saturated $NaHCO_3$ solution, is dried over $Na_2SO_4$ and concentrated. The cleaning takes place by column chromatography with $CHCl_3$/ethyl acetate 1:2.

Characterization

| | | |
|---|---|---|
| $^1$H-NMR ($CDCl_3$) | : | 1.50 (m, 8H); 1.75 (m, 4H); 1.85 (m, 4H); 3.70 (m, 8H); 3.90 (t, 4H); 4.05 (t, 4H); 4.20 (t, 4H); 4.25 (t, 4H); 5.85 (dd, 2H); 6.15 (dd, 2H); 6.40 (dd, 2H); 6.95 (d; 4H); 7.00 (d, 4H); 7.25 (s, 8H); 8.15 (d, 8H) ppm |
| $^{13}$C-NMR ($CDCl_3$) | : | 25.6; 28.4; 28.9; 64.4; 67.6; 68.0; 69.4; 70.6; 70.8; 114.2; 114.4; 121.4; 121.7; 122.5; 128.5; 130.5; 132.2;148.3; 163.1; 163.4; 164.6; 164.7; 166.2 ppm |
| IR (KBr) | : | 2936; 1730; 1606; 1511; 1259; 1166; 1072; 762 cm$^{-1}$ |

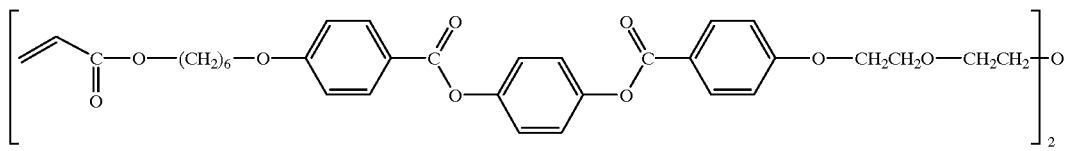

| | | |
|---|---|---|
| -continued | | |
| Polarization microscope[1]) | : | k 111 n 194 i |
| DSC[1]) | : | k 106 n 179 i (2nd heating) |
| Polarization microscope[1]) | : | k 111 n 194 i |
| DSC[1]) | : | k 106 n 179 i (2nd heating) |

Figure 4:
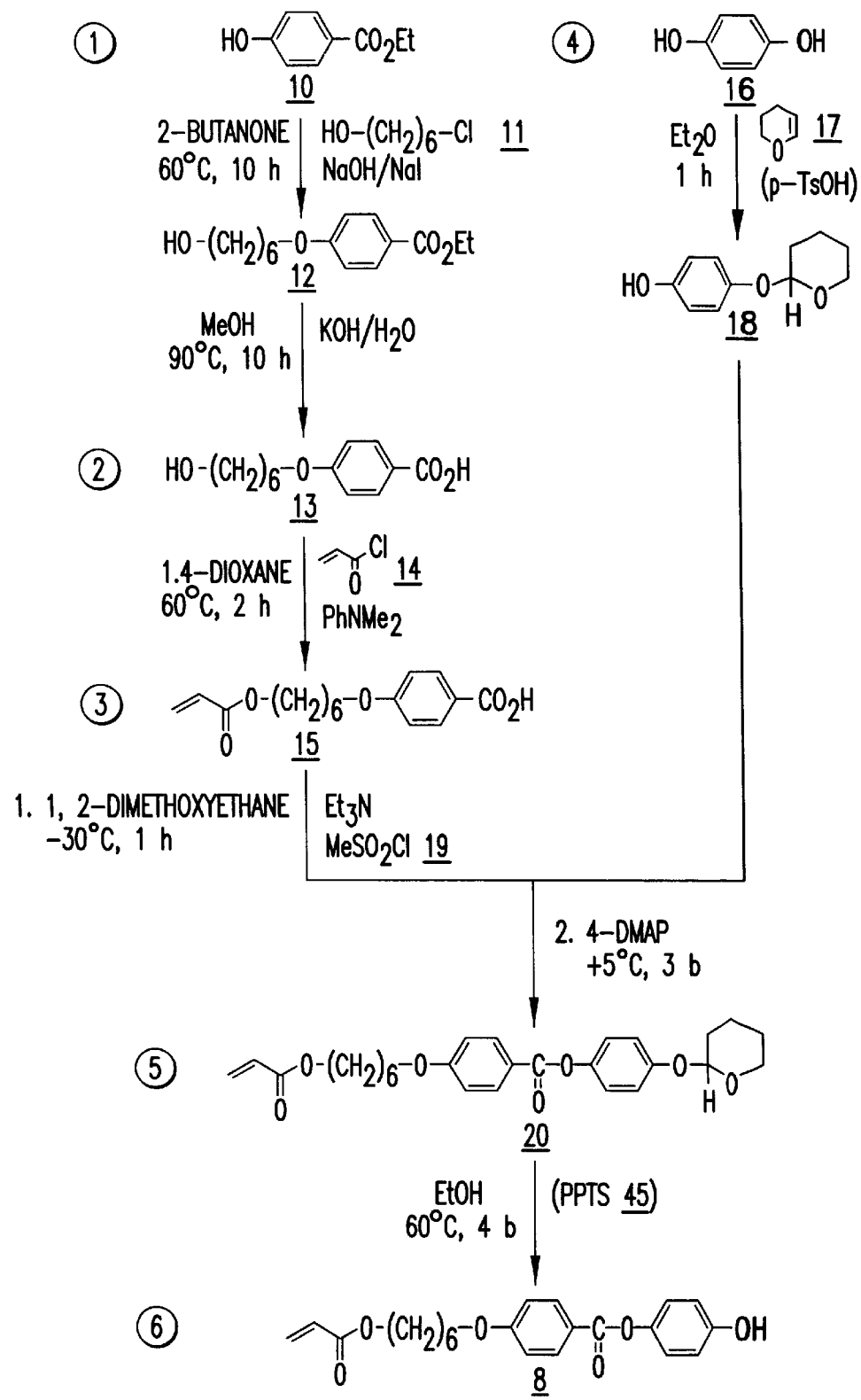
FIG. 4 is a schematic representation of the synthesis for a first embodiment of a three-core twin nemate with an alkyl side chain.
Figure 5:
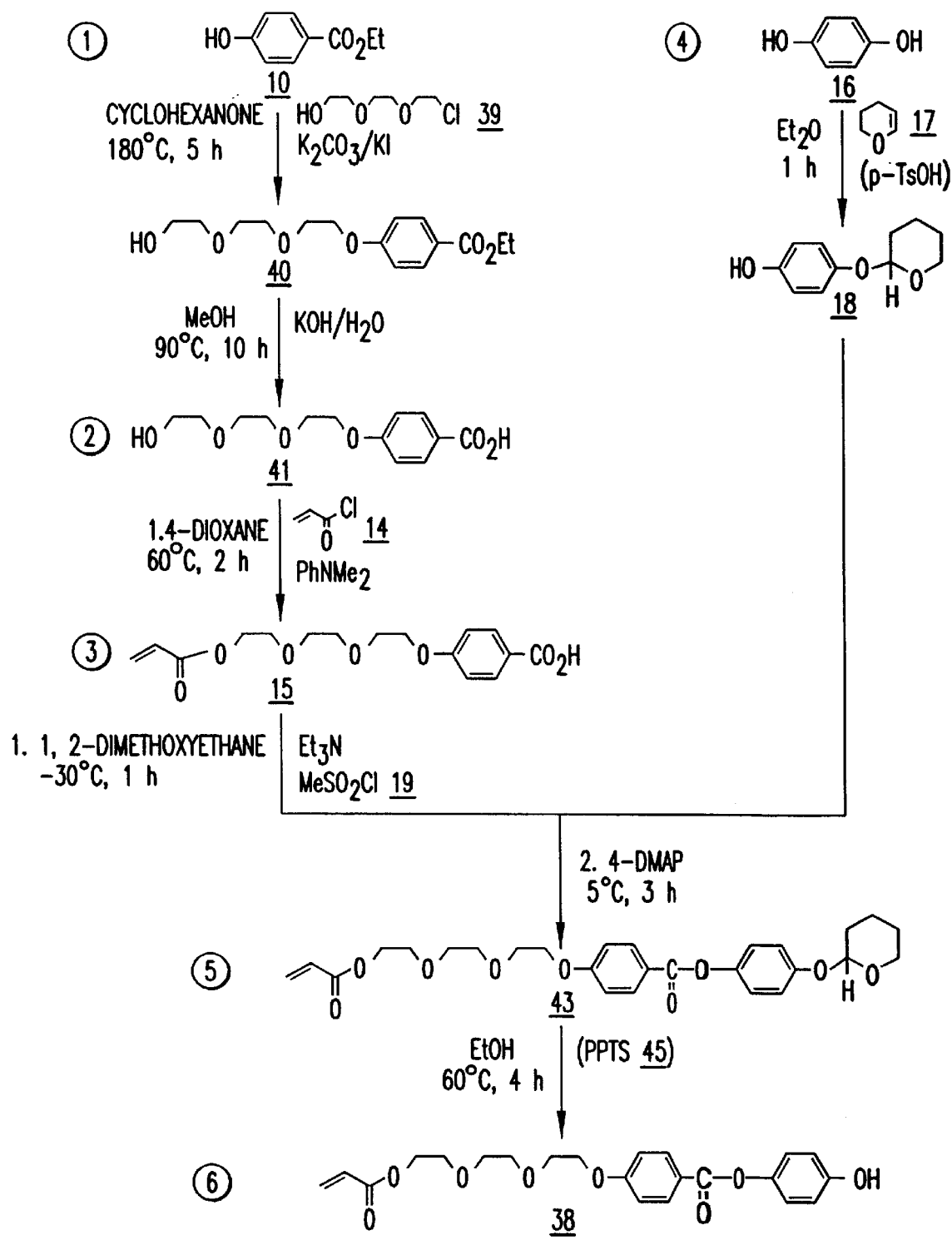
FIG. 5 is a schematic representation of the synthesis for a first embodiment of a three-core twin nemate with an alkyl side chain.

The preliminary stages are synthesized by means of the diagrams illustrated in FIGS. 4 and 5. The synthesis of the mesogen with the alkyl side chain (FIG. 4) takes place according to D. J. Broer, J. Boven, G. N. Mol, G. Challa, *Makromol. Chem.* 190, 2255 (1989) and S. Jahromi, J. Lub, G. N. Mol, *Polymer* 35 622 (1994). The synthesis of the flexible tetraethylene glycol spacer (FIG. 5) takes place analogously to the general specifications according to B. Otterholm, C. Alstermark, K. Flatischler, S. T. Lagerwall, K. Skarp, *Mol. Cryst. Liq. Cryst.* 146, 189 (1987) (Step 1) and J. M. G. Cowie, *Makromol. Chem.* 191, 1393 (1990) and J. M. G. Cowie, *Makromol. Chem.* 192, 143 (1991).

EXAMPLES, 2, 3 and 4

Three additional embodiments of the present invention have the following structure:

according to Example 2 (with the vanillin unit on the outside) melts during the first heating at 76° C. (Smp. 1) and 88° C. (Smp. 2) and clarifies at 114° C. During the cooling, a nematic phase occurs starting at 110° C. and a glass transition occurs at −9° C. During the second heating, in addition to a glass transition at −2° C. and the clarification point at 114° C., another small peak can be detected at 88° C. The substance is probably slowly crystallizing again.

The compound according to Example 3 (with the vanillin unit on the inside), in contrast to the above compound, shows no glass transition:

2nd heating k 93 n 126 i

2nd cooling k 53 n 121 i

The compound according to Example 4 (with two vanillin units) first melts over several stages. During the cooling, an LC-phase forms starting at 46° C. and a glass transition occurs at 0° C. Here, the addition of chiral constituents can cause a reinforcing effect with respect to the liquid-crystalline characteristics.

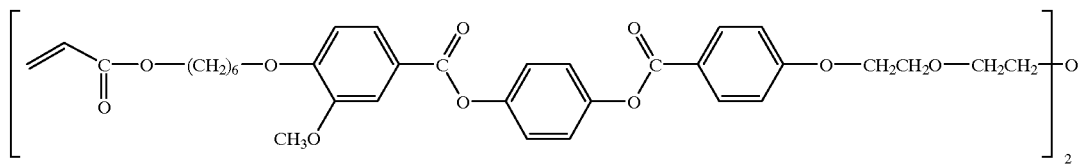

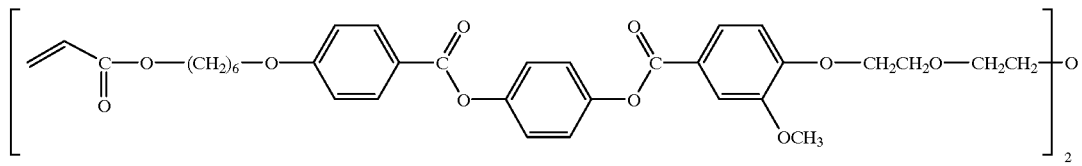

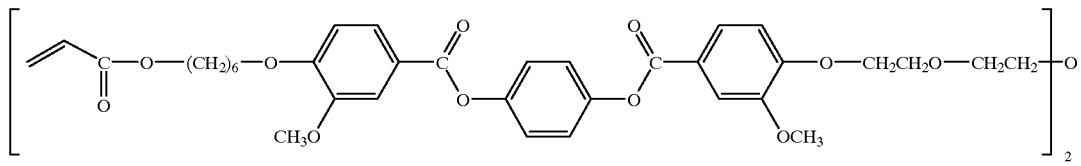

They differ from the twin nemate 1 only in that they have one or two vanillin units; thus are methoxylated one or two aromatic group. These compounds are produced analogously to the above-described procedure. The compound

EXAMPLE 5

Another embodiment of the present invention has the following structure:

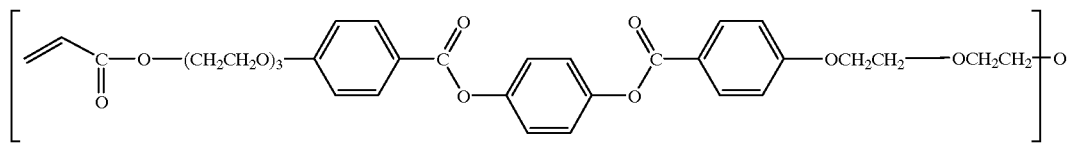

(Twin Nemate 2)

Figure 6:
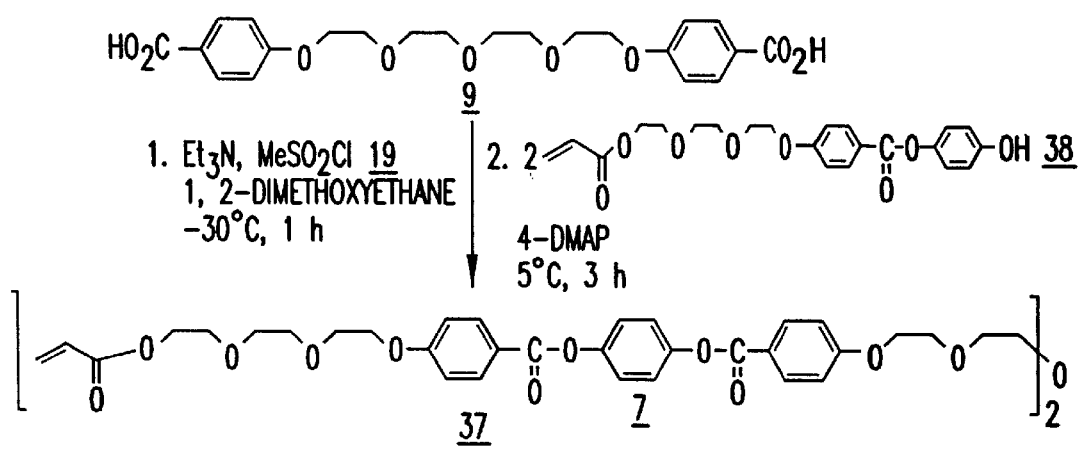
FIG. 6 is a schematic representation of the synthesis of another embodiment of a three-core twin-nemate with an ethylene oxide side chain.

According to the diagram illustrated in FIG. 6, the twin nemate 2 can be synthesized as follows:

1.42 g (0.0033 mol) tetraethylene glycol-1,13-bis-(4-benzoic acid) are reduced to slurry in 80 ml 1,2-dimethoxy ethane and, after the addition of 1.83 ml (0.0131 mol) triethylamine, are cooled to −30° C. At −30° C., 0.51 ml (0.0065 mol) methane sulfonic acid chloride are added in drops and stirring takes place for 1 h. After the addition of 3.00 g (0.0072 mol) mesogen with an ethylene oxide side chain, 0.08 g (6.5×10$^{-4}$ mol) 4-dimethylamino pyridine and 50 mg 2,6-Di-tert-butyl-p-cresol, the mixture is stirred for another 3 h at 5° C.

Subsequently, the formed precipitation is filtered off, is washed twice with 20 ml of 1,2-dimethoxy ethane, and the filtrate is concentrated in the WV. The residue is recrystallized twice in ethanol. The continued cleaning takes place by chromatography by way of silica gel with $CHCl_3$/acetone 2:1 as the flow agent and precipitating in hexane. A yield of 183 g (45%) is obtained.

Characterization

| | |
|---|---|
| $^1$H-NMR (CDCl$_3$) | : 3.70 (m, 20H); 3.89 (t, 8H); 4.20 (t, 8H); 4.32 (t, 4H); 5.82 (dd, 2H); 6.14 (dd, 2H), 6.42 (dd, 2H); 7.00 (d, 8H); 7.28 (s, H), 8.13 (d, 8H) ppm |
| $^{13}$C-NMR (CDCl$_3$) | : 63.5; 67.6; 69.1; 69.5; 70.6; 70.8; 114.3; 121.7; 122.5; 128.2; 130.9; 132.2; 148.3; 163.1; 164.6; 116.0 ppm |
| IR (KBr) | : 2880; 1727; 1606; 1513; 2454; 1264; 1041; 850; 767 cm$^{-1}$ |
| Polarization Microscope[1] | : k 95 n 153 i |
| DSC[2] | : k 94 n 131 i (2nd heating) |

Figure 7:
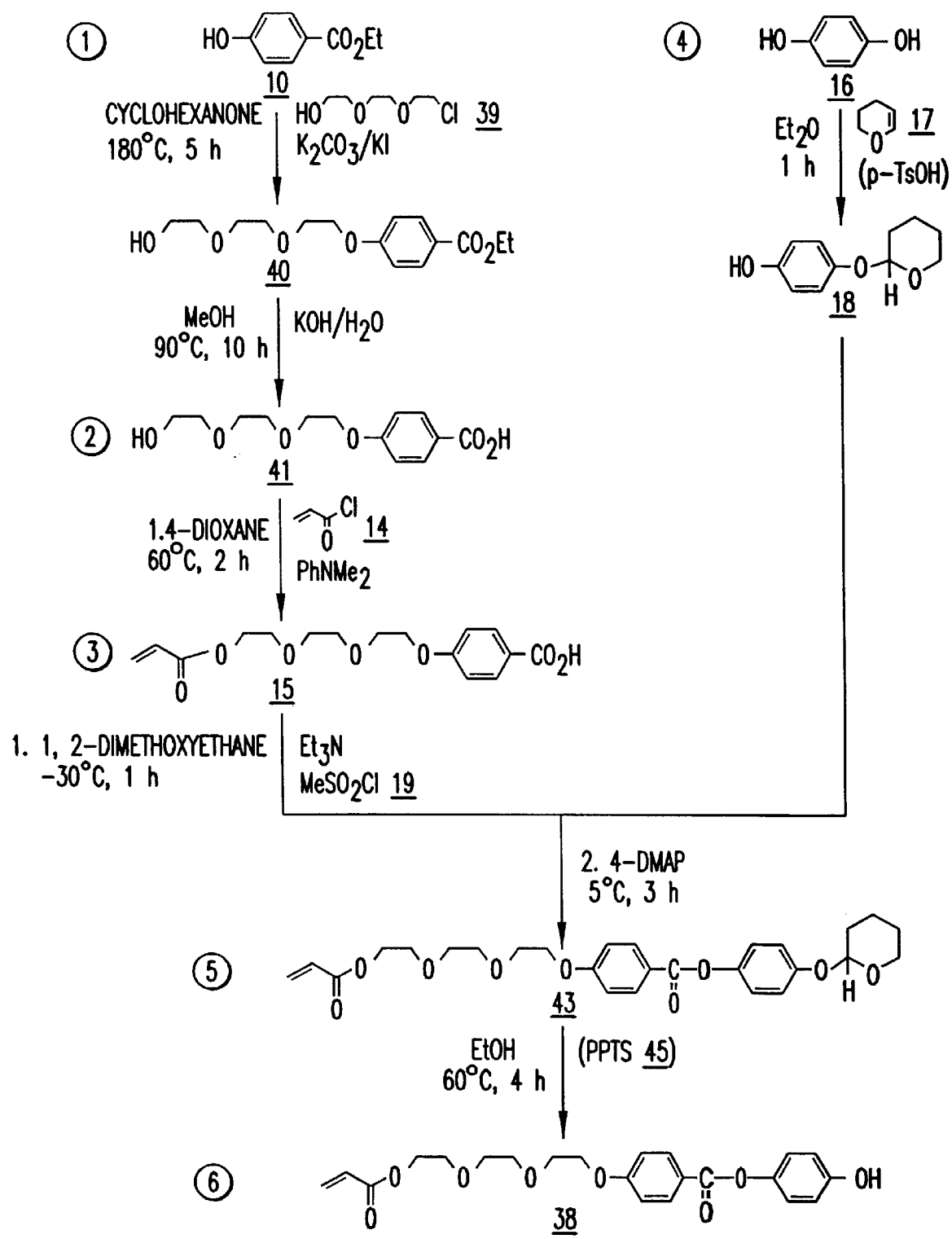
FIG. 7 is a schematic representation of the synthesis of another embodiment of a three-core twin-nemate with an ethylene oxide side chain.

1) 2% by weight as a stabilizer, 10 K/min
2) 2% by weight as a stabilizer, 2nd heating 10 K/min. 2nd cooling 40 K/min The synthesis of the preliminary stages takes place by means of the diagrams illustrated in FIGS. 5 and 7. The synthesis course of the mesogen with the ethylene oxide side chain is analogously described as the general specification in S. Hünig, G. Mäkl, J. Sauer, in "Integrated Organic Workshop", Publishers Chemie, Weinheim 1979 (Step 1); S. Jahromi, J. Lub, G. N. Mol, in *Polymers* 35, 622 (1994) (Step 4); and D. J. Broer, J. Boven, G. N. Mol, G. Challa, in *Macromol. Chem.* 190, 2255 (1989).

EXAMPLE 6

Another embodiment of the present invention has the following structure (Twin Nemate 3)

Figure 8A:
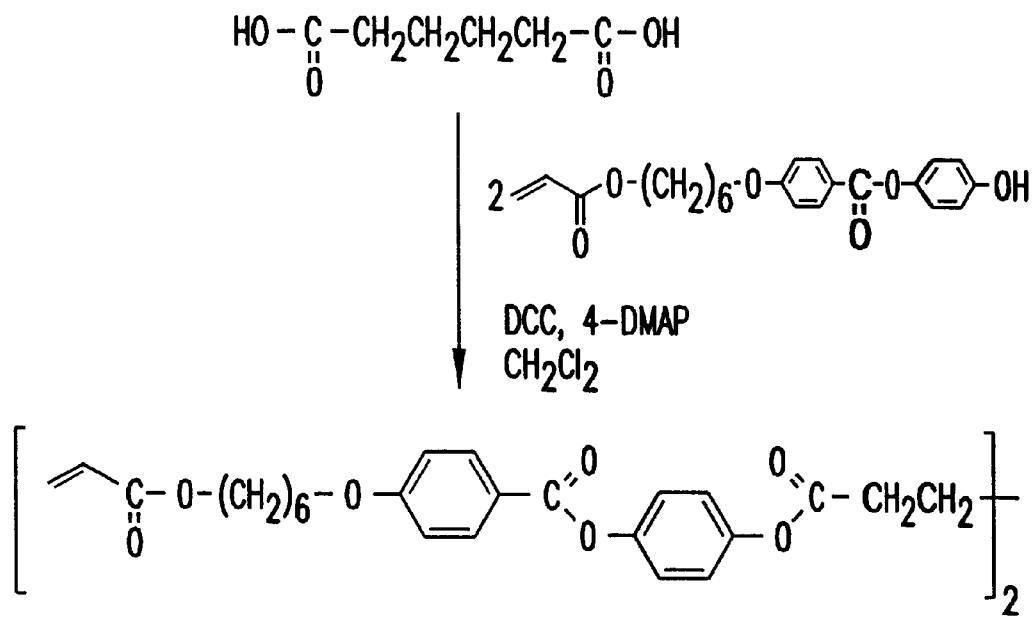
FIG. 8a is a schematic representation of the synthesis of an embodiment of a two-core twin nemate with an alkyl side chain.

The synthesis takes place according to the diagram illustrated in FIG. 8a.

0.55 g (3.75 mmol) adipinic acid are reduced to slurry in 50 ml $CH_2Cl_2$ and mixed with 2.88 g (7.50 mmol) mesogen with an alkyl side chain, 0.09 g (0.75 mmol) 4-dimethylamino pyridine and 50 mg 2,6-Di-tert-butyl-p-cresol as the stabilizer. This mixture is cooled to 0° C. and 186 g (9.00 mmol) N,N-Dicyclohexyl carbodiimide are added. After a stirring for 1 h at 0° C., the ice bath is removed and the stirring is continued for another 16 h at room temperature.

Subsequently, the formed precipitation is filtered off, is washed again with a little $CH_2Cl_2$, and the solvent is concentrated. The residue is received in 100 ml $CH_2C_2$, a precipitation again taking place, which must be filtered off. The $CH_2Cl_2$-phase is now washed twice with 25 ml of 2N HCL and twice with 25 ml of a saturated $NaHCO_3$-solution. The residue is dried over $Na_2SO_4$ and the solvent is concentrated. For a further cleaning, a column chromatography is carried out with $CHCl_3$/ethyl acetate 30:1 as the flow medium and the residue is recrystallized in 15 ml 1-butanol. 1.61 g (49%) twin nemate 3 is obtained in the form of white crystals.

Figure 8B:
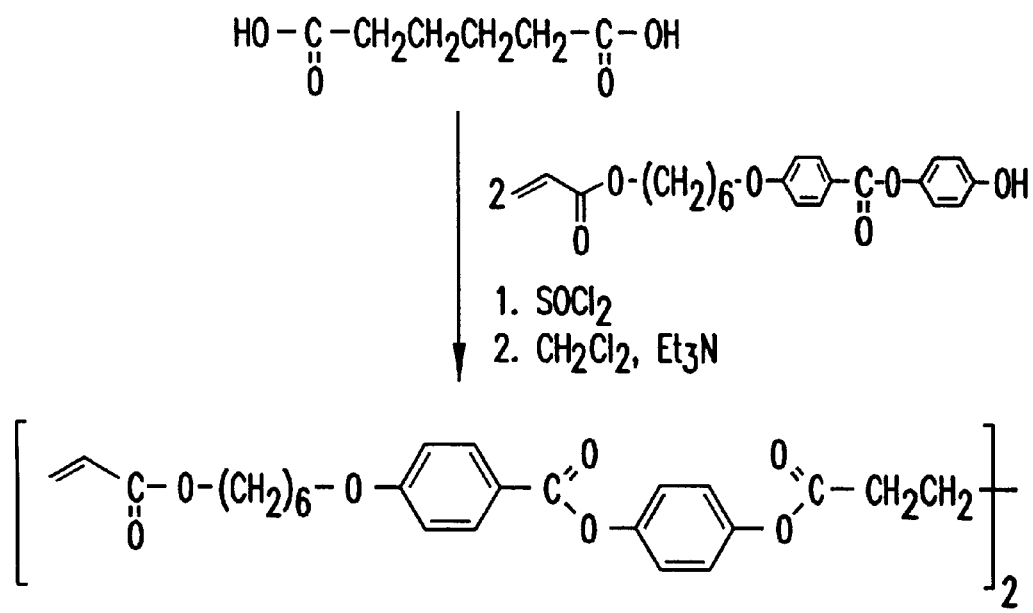
FIG. 8b is a schematic representation of the synthesis of an embodiment of a two-core twin nemate with an alkyl side chain.

Another synthesis course is illustrated in FIG. 8b.

After the addition of 20 ml $SOCl_2$ and 3 drops of DMF, 10.45 g (0.06 mol) of octanedioic acid are boiled for 2 hours under a reflux. Excess $SOCl_2$ is first withdrawn on the water jet vacuum and then on the high-vacuum pump. The red oily residue is distilled. 11.72 g of a colorless liquid are obtained.

1.54 (0.004 mol) mesogen (=4-(6-acryloyloxy-hexyloxy) benzoic acid-4'-hydroxy phenyl ester), 0.7 ml (0.05 mol) $Et_3N$ and 50 mg 2,6-Di-tert.butyl-p-cresol are dissolved in 30 ml $CH_2Cl_2$ and cooled to 0° C. At 0° C., 0.38 g (0.0018 mol) octanedioic acid chloride in 5 ml $CH_2Cl_2$ are carefully added in drops. Then the ice bath is removed and stirring takes place overnight at room temperature.

The reaction mixture is fed to 15 ml ice-cooled 2NHCL. The $CH_2Cl_2$-phase is separated and is washed with 15 ml of a saturated NaCl-solution, is dried over $Na_2SO_4$ and is concentrated. The further cleaning takes place by means of column chromatography ($CHCl_3$/ethyl acetate 30:1). 1.03 g (63% of a white solid is obtained.

The compound is nematic. The DSC data are k 110 n 195 i (with 1% by weight sulfur in dioxane freeze-dried; thermal value 10 K/min).

Here also, the synthesis of the preliminary stages takes place as described above (compare FIG. 4).

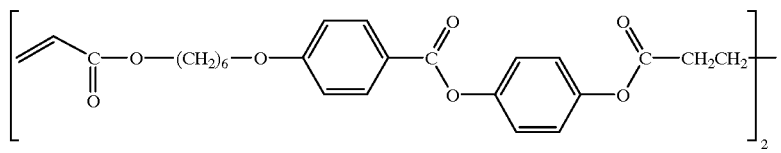

EXAMPLE 7, 8

Two other embodiments of the present invention have the following structure:

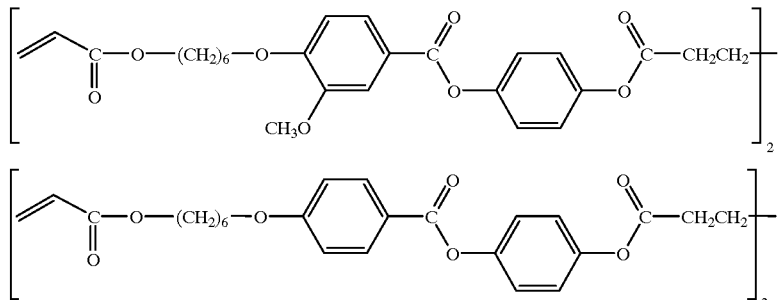

These are variants of the compound according to Example 6 with an additional methoxy group (or vanillin unit) or with a tetraethylene glycol spacer. Although the compound with the vanillin unit shows no clearly pronounced liquid-crystalline characteristics, these can be reinforced by the copolymerization of chiral constituents. The compound with the C6 side chain and the tetraethylene glycol spacer in the center is nematic at room temperature. It melts during the first heating at 53° C. and during the cooling forms a nematic phase between 33° C. and 8° C. (no glass transition). During the second heating, the compound melts at 4° C.; then exhibits several transitions, and clarifies at 37° C. The second cooling is analogous to the first cooling.

As an example, three synthesis courses for the compounds according to the invention are obtained from the above:

1) with 1,2-dimethoxy ethane, $Me_2SO_2Cl$ and $Et_3N$, wherein 4-DMAP is added as the catalyst;
2) with $CH_2Cl_2$ and DCC; and
3) with $SOCl_2$ and $Et_3N$.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for manufacturing a nematic liquid-crystalline polymer, comprising polymerizing identical or different monomers of the general formula $C-A_m$ to form said liquid-crystalline polymer, wherein $m \geq 2$, such that when m=2, C is a radical of the general formula $C_nH_{2n}$, in which n is a whole number from 1 to 40 and at least one methylene group may be substituted by oxygen or at least one hydrogen may be substituted by alkyl or alkoxy groups, said alkyl or alkoxy groups having 1 to 20 carbon atoms, when m>2, C is selected from the group consisting of oligopropylene oxide, oligobutylene oxide, branched alkyls with 4 to 40 Carbon atoms, trimethylol propane, pentaerythrite, cyclohexane tricarboxylic acid, cyclohexane triole, aromatic carboxylic acids with two carboxyl groups and phenolene with at least two —OH groups, wherein A are identical or different radicals of the general formula Y—B—M, wherein Y is an acrylate, methacrylate, vinyl ether, epoxide or azide radical, B are identical or different radicals of the general formula $C_nH_{2n}$ in which n is a whole number from 0 to 20 and at least one methylene group may be substituted by oxygen, and M has the general formula
$R^1-X^1-R^2-X^2-R^3-X^3-R^4-$, wherein
$R^1$, $R^2$, $R^3$ and $R^4$ are identical or different radicals selected from the group consisting of —O—, —COO—, —CONH—, —CO—, —S—, —C≡C—, —CH=CH—, —CH=N—, —CH$_2$—, —N=N—, and —N=N(O) and $R^2$ —$X^2$—$R^3$, $X^3$—$R^4$ or $R^2$—$X^2$—$R^3$—$X^3$ may be a C—C bond, $X^1$, $X^2$, and $X^3$ are identical or different radicals selected from the group consisting of:

1,2-, 1,3- or 1,4-phenylene;
1,2-, 1,3- or 1,4-cyclohexene;
an aryl alkane or heteroaryl alkane having 6 to 10 atoms in the ring structure and containing 1 to 3 heteroatoms selected from the group consisting of O, N, and S; and
a cycloalkylene having 3 to 10 carbon atoms,
wherein said aryl alkane, heteroaryl alkane and cycloalkylene are substituted with at least one identical or different substituent selected from the group consisting of —H, linear or branched $C_1$- to $C_{20}$-alkyl, $C_1$- to $C_{20}$-alkoxy, $C_1$- to $C_{20}$-alkylthio, $C_1$- to $C_{20}$-alkylcarbonyl, $C_1$- to $C_{20}$-alkoxycarbonyl, $C_1$- to $C_{20}$-alkylthiocarbonyl, —OH, —F, —Cl, —Br, —I, —CN, —NO$_2$, cycloalkyl, formyl, and linear or branched alkyl, alkoxy or alkylthio radicals with 1 to 20 carbon atoms which are interrupted by ether oxygen, thioether sulfur or ester groups.

2. A process according to claim 1, wherein the polymerization is induced radically or cationically.

3. A process according to claim 2, wherein the polymerization is induced using at least one polymerization initiator.

4. A process according to claim 3, wherein the polymerization initiator is a radical photoinitiator.

5. A process according to claim 4, wherein the radical photoinitiator is selected from the group consisting of acetophenones, diazonium compounds, peroxides, and mixtures thereof.

6. A process according to claim 3, wherein the radical photoinitiator is present in a concentration from 1 to 5 molar %.

7. A process according to claim 3, wherein the photoinitiator is a cationic photoinitiator selected from the group consisting of diaryl sulfonium salts, diaryl iodonium salts, and mixtures thereof.

8. A process according to claim 7, wherein the cationic photoinitiator is present in a concentration from 0.5 to 10% by weight.

9. A process according to claim 1, further comprising adding a reaction control substance in a concentration of from 1 to 10 molar %.

10. A process according to claim 9, wherein the reaction control substance is 1-capric thiole.

11. A process according to claim 1, wherein the polymerization reaction is induced by ultraviolet radiation or the reaction product is postcured by a thermal treatment, or both.

12. A process according to claim 1, further comprising carrying out the polymerization reaction in the presence of at least one additional compound of the general formula of at least one of $Y^3—B^3—M^2—B^4—Y^4$ and $(Y^3—B^3)_n—M^2—B^4—Y^4$,
wherein n is equal to 2 or 3, $Y^3$ is an acrylate, methacrylate, vinyl ether, epoxide or azide radical and $Y^4$ is an acrylate, methacrylate, vinyl ether, epoxide or azide radical or a non-polymerizable radical selected from the group consisting of —H, —CN and a cholesteryl group, $B^3$ and $B^4$ are identical or different radicals of the general formula $C_nH_{2n}$, wherein n is a whole number from 0 to 20 and at least one methylene group may be substituted by oxygen, M has the general formula $—R^5—X^4—R^6—X^5—R^7—X^6—R^8$, wherein $R^5$, $R^6$, $R^7$, and $R^8$ are identical or different double-bonding radicals selected from the group consisting of —O—, —COO—, —CONH, —CO—, —S—, —C≡C—, —CH=CH—, —CH=N—, —CH$_2$—, —N=N—, and —N=N(O) and $R^6—X^5—R^7$ or $R^6—X^5—R^7—X^6$ may also be a C—C bond, $X^4$, $X^5$ and $X^6$ are identical or different radicals selected from the group consisting of:

1,2-, 1,3- or 1,4-phenylene;

1,2-, 1,3- or 1,4-cyclohexene;

an aryl alkane having with 6 to 10 atoms in the ring structure and containing 1 to 3 heteroatoms selected from the group consisting of O, N, and S, and a cycloalkylene having 3 to 10 carbon atoms, wherein said aryl alkane and said cycloalkylene are substituted with at least one identical or different substituent selected from the group consisting of —H, linear or branched $C_1$- to $C_{20}$-alkyl, $C_1$- to $C_{20}$-alkoxy, $C_1$- to $C_{20}$-alkylthio, $C_1$- to $C_{20}$-alkylcarbonyl, $C_1$- to $C_{20}$-alkoxycarbonyl, $C_1$- to $C_{20}$-alkylthiocarbonyl, —OH, —F, —Cl, —Br, —I, —CN, —NO$_2$, cycloalkyl, formyl, and linear or branched alkyl, alkoxy or alkylthio radicals with 1 to 20 carbon atoms which are interrupted by oxygen, thioether sulfur or ester groups.

13. A process according to claim 12, wherein the at least one $B^3$ and $B^4$ are chiral.

14. A process according to claim 1, wherein said monomers have a mol mass of from 1,000 to 3,000 g/mol.

15. A process according to claim 1, in which the C radical is a tetraethylene glycol radical, a butyl radical or a hexyl radical.

16. A process according to claim 1, wherein at least one of the B radicals is a hexyl or ethylene oxide radical.

17. A process according to claim 1, further comprising adding a chiral constituent with one or more of said monomers to form a mixture, thereby forming a cholesteric liquid crystalline polymer upon polymerization.

18. A liquid crystalline polymer produced by polymerization of at least one compound according to claim 1.

19. A process for manufacturing a nematic liquid-crystalline polymer consisting of polymerizing monomers of the general formula $C—A_m$,
wherein $m \geq 2$, such that when m=2, C is a radical of the general formula $C_nH_{2n}$, in which n is a whole number from 1 to 40 and at least one methylene group may be substituted by oxygen or at least one hydrogen may be substituted by alkyl or alkoxy groups, said alkyl or alkoxy groups having 1 to 20 carbon atoms, when m>2, C is selected from the group consisting of oligopropylene oxide, oligobutylene oxide, branched alkyls with 4 to 40 Carbon atoms, trimethylol propane, pentaerythrite, cyclohexane tricarboxylic acid, cyclohexane triole, aromatic carboxylic acids with two carboxyl groups and phenolene with at least two —OH groups, wherein A are identical or different radicals of the general formula Y—B—M, Y is an acrylate, methacrylate, vinyl ether, epoxide or azide radical, B are identical or different radicals of the general formula $C_nH_{2n}$ in which n is a whole number from 0 to 20 and at least one methylene group may be substituted by oxygen, and M has the general formula
$R^1—X^1—R^2—X^2—R^3—X^3—R^4—$, wherein $R^1$, $R^2$, $R^3$ and $R^4$ are identical or different radicals selected from the group consisting of —O—, —COO—, —CONH, —CO—, —S—, —C≡C—, —CH=CH—, —CH=N—, —CH$_2$—, —N=N—, and —N=N(O) and $R^2$ —$X^2—R^3$, $X^3—R^4$ or $R^2—X^2—R^3—X^3$ may be a C—C bond, $X^1$, $X^2$, and $X^3$ are identical or different radicals selected from the group consisting of:

1,2-, 1,3- or 1,4-phenylene;

1,2-, 1,3- or 1,4-cyclohexene;

an aryl alkane or heteroaryl alkane having 6 to 10 atoms in the ring structure and containing 1 to 3 heteroatoms selected from the group consisting of O, N, and S; and a cycloalkylene having 3 to 10 carbon atoms, wherein said aryl alkane, heteroaryl alkane and cycloalkylene are substituted with at least one identical or different substituent selected from the group consisting of —H, linear or branched $C_1$- to $C_{20}$-alkyl, $C_1$- to $C_{20}$-alkoxy, $C_1$- to $C_{20}$-alkylthio, $C_1$- to $C_{20}$-alkylcarbonyl, $C_1$- to $C_{20}$-alkoxycarbonyl, $C_1$- to $C_{20}$-alkylthiocarbonyl, —OH, —F, —Cl, —Br, —I, —CN, —NO$_2$, cycloalkyl, formyl, and linear or branched alkyl, alkoxy or alkylthio radicals with 1 to 20 carbon atoms which are interrupted by ether oxygen, thioether sulfur or ester groups.

* * * * *